United States Patent [19]
Burdette et al.

[11] Patent Number: 5,522,869
[45] Date of Patent: Jun. 4, 1996

[54] ULTRASOUND DEVICE FOR USE IN A THERMOTHERAPY APPARATUS

[76] Inventors: Everette C. Burdette, 2115 Seaton Ct., Champaign, Ill. 61821; Goran K. Svensson, 77 Brush Hill Rd., Sherborn, Mass. 01770; Xing-Qi Lu, 1341 Walnut St., Newton, Mass. 02161; Michael H. Slayton, 1335 E. Louis Way, Tempe, Ariz. 85284

[21] Appl. No.: 399,063

[22] Filed: Mar. 8, 1995

Related U.S. Application Data

[63] Continuation of Ser. No. 245,301, May 17, 1994.

[51] Int. Cl.⁶ .................................................. A61N 1/00
[52] U.S. Cl. ........................ 607/97; 310/322; 310/334; 310/369
[58] Field of Search ................................ 128/915, 916, 128/660.03, 661.02; 607/97; 310/315, 322, 334, 341, 369

[56] References Cited

U.S. PATENT DOCUMENTS

| | | | |
|---|---|---|---|
| 4,823,041 | 4/1989 | Inoue et al. | 310/322 |
| 4,889,122 | 12/1989 | Watmough et al. | 607/97 |
| 5,103,130 | 4/1992 | Rolt et al. | 310/322 |
| 5,316,000 | 5/1994 | Chapelon et al. | 607/97 |

FOREIGN PATENT DOCUMENTS

9417514  8/1994  WIPO ..................................... 607/97

*Primary Examiner*—Angela D. Sykes
*Assistant Examiner*—Robert L. Nasser, Jr.
*Attorney, Agent, or Firm*—Reinhart, Boerner, Van Deuren, Norris & Rieselbach

[57] ABSTRACT

A thermotherapy device for use in treating cancer. The thermotherapy device includes a radio frequency power source for energizing transducers to output ultrasound waves to heat a patient treatment site. The transducers are arranged in a cylindrical shape to treat the patient and a variable number of ultrasound transducers can provide a customized therapy treatment.

20 Claims, 9 Drawing Sheets

| NUMBER OF TRANSDUCERS | RING NUMBER |
|---|---|
| 48 | 1 |
| 48 | 2 |
| 48 | 3 |
| 48 | 4 |
| 48 | 5 |
| 24 | 6 |
| 24 | 7 |
| 16 | 8 |
| 16 | 9 |

| NUMBER OF TRANSDUCERS | RING NUMBER |
|---|---|
| 48 | 1 |
| 48 | 2 |
| 48 | 3 |
| 48 | 4 |
| 48 | 5 |
| 24 | 6 |
| 24 | 7 |
| 16 | 8 |
| 16 | 9 |

ULTRASOUND DEVICE FOR USE IN A THERMOTHERAPY APPARATUS

This is a continuation of copending application Ser. No. 08/245,301 filed on May 17, 1994.

The present invention is directed generally to a system for providing thermotherapy treatment of breast cancer. More particularly, the invention is concerned with a cylindrical ultrasound applicator having a plurality of cylindrical transducer bands or rings for controllably applying ultrasound to a patient's breast as part of a thermotherapy treatment procedure. The cylindrical transducers also can be used by virtue of pulse echo methods to sense the potentially changing position of the patient's breast in the treatment cylinder.

Conventional treatment of breast cancer involves radical procedures such as massive radiation therapy, chemotherapy and extensive surgery. Such procedures often lead to substantial side effects and disfigurement. In view of the large number of cases of breast cancer and the substantial negative effects of current methodologies of treatment, there is a general need for an improved technique of treatment for breast cancer. Moreover, specific types of breast cancer, such as localized, advanced cases are not usually candidates for breast conserving therapy and intraductal cancers have higher recurrence rates than other breast cancers using conventional therapies.

It is, therefore, an object of the invention to provide an improved method and apparatus for treatment of breast cancer.

It is another object of the invention to provide a novel method and apparatus for thermotherapy treatment of breast cancer.

It is a further object of the invention to provide an improved method of use and apparatus using an improved ultrasound applicator for performing thermotherapy treatment of breast cancer.

It is an additional object of the invention to provide a novel method of use and apparatus using a cylindrical transducer array for generating ultrasound energy for thermotherapy treatment.

It is still another object of the invention to provide an improved method of use and apparatus having a modular ultrasound applicator configured to apply ultrasound energy, measure power applied therapeutically and also to measure the position of the patient's breast by ultrasound pulse echo techniques.

It is yet a further object of the invention to provide a novel method of use and apparatus using a cylindrical stack of ultrasound transducer rings to apply energy to a subject patient's diseased breast and monitoring power application by computer controls.

It is also an object of the invention to provide an improved method of use and apparatus including a thermotherapy treatment table having an opening enabling disposition of a diseased breast within a water containing cylindrical treatment housing.

It is yet an additional object of the invention to provide a novel method of use and apparatus for treatment of intraductal cancers and advanced, localized breast cancers.

These and other objects, features and advantages of the present invention will be readily apparent from the following description of the preferred embodiments thereof, taken in conjunction with the accompanying drawings described below wherein like elements have like numerals throughout the several views.

DETAILED DESCRIPTION OF PREFERRED EMBODIMENTS

Figure 1:
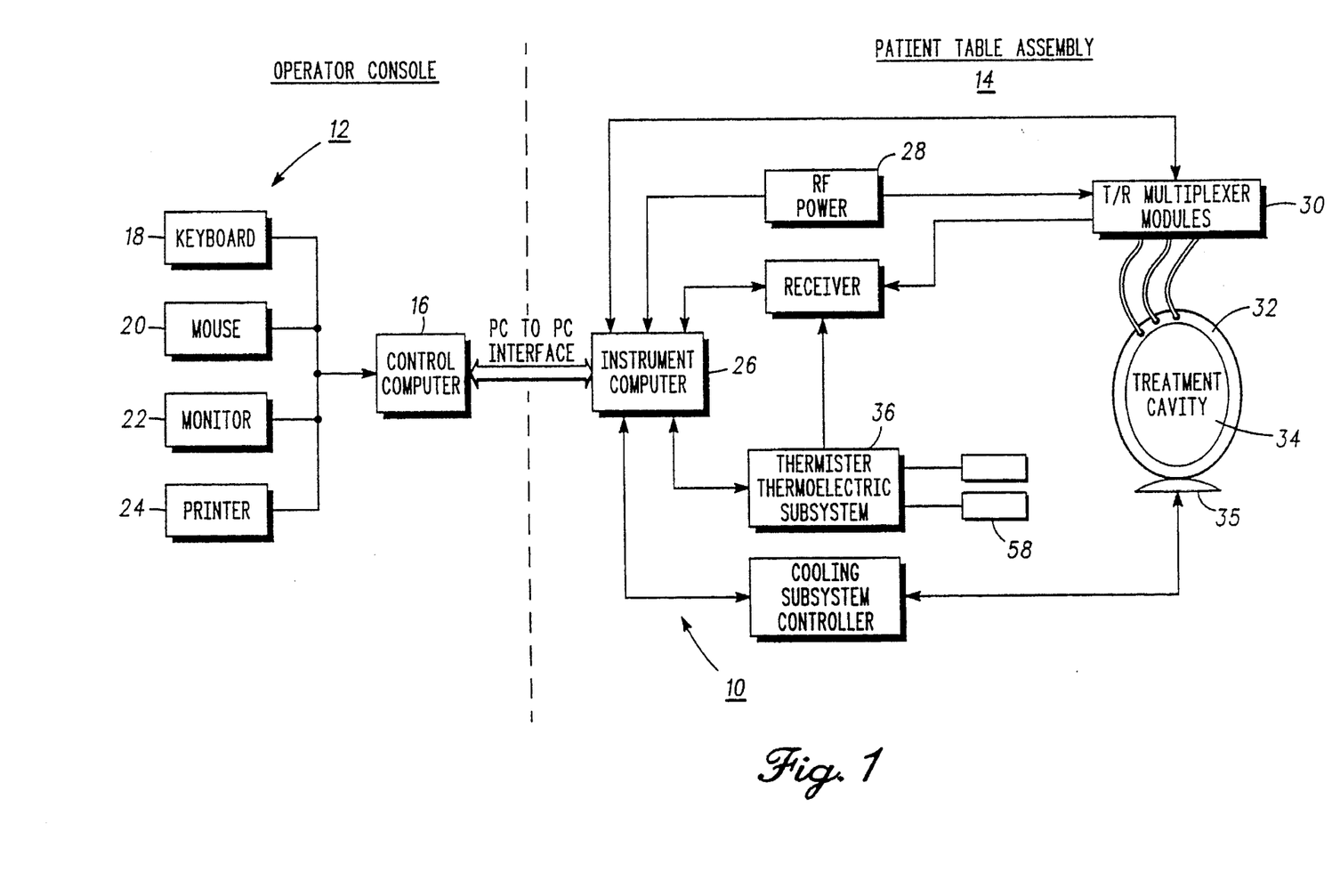
FIG. 1, illustrates a block diagram of a thermotherapy treatment system.
Figure 2A:
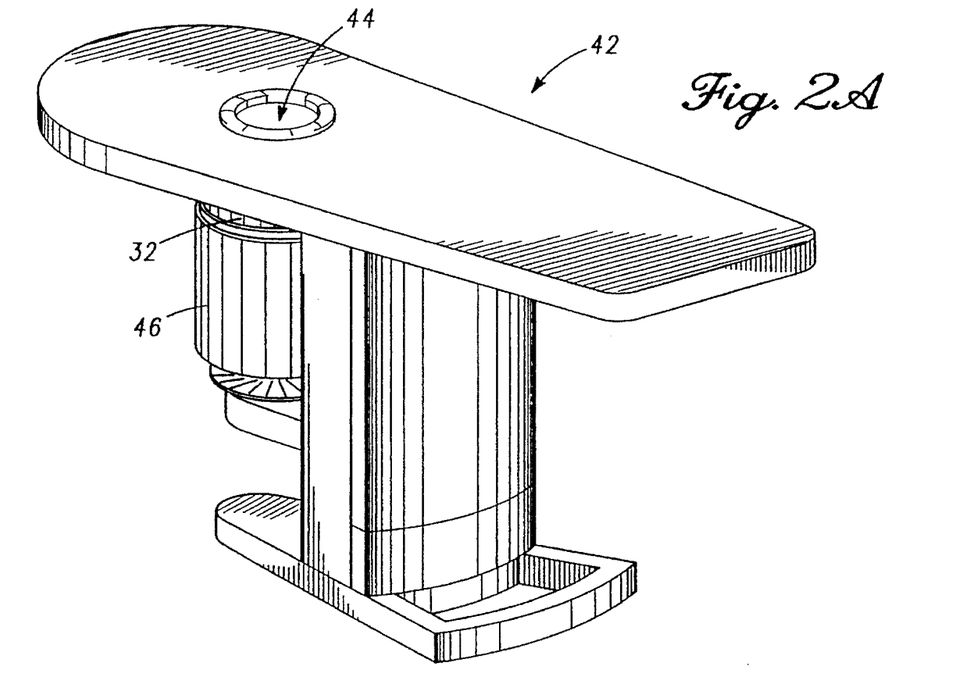
FIG. 2A illustrates a rear perspective view of a thermotherapy treatment table and FIG. 2B illustrates a front perspective view of the thermotherapy treatment table.
Figure 2B:
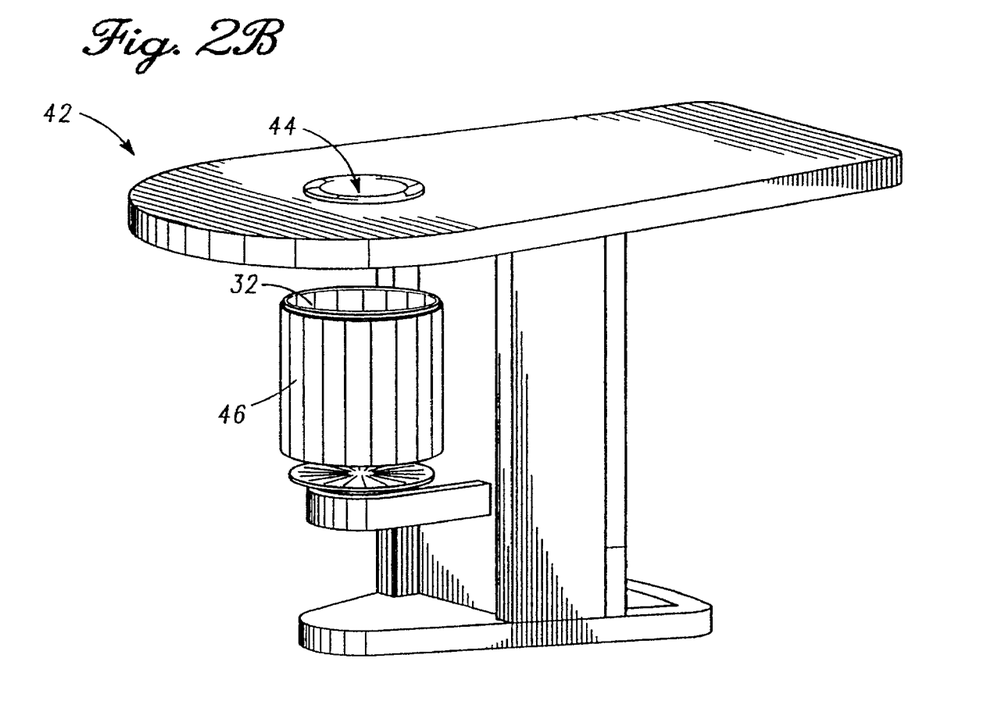

A thermotherapy treatment apparatus constructed in accordance with the invention is shown in the figures generally at 10. In particular, referring to FIS. 1 and 2, the system 10 includes an operator console 12 and a patient treatment table system 14. The operator console 12 includes a control computer 16 (such as a conventional Pentium PC/AT with 16 MB RAM) coupled on the input side to a keyboard 18, mouse 20, monitor 22 and printer 24. On the output side of the operator console 12 is an instrument computer 26 (such as the above named control computer example) which operates on power and temperature control signals to control the thermotherapy treatment provided. The instrument computer 26 thus operates in conjunction with an RF power subsystem 28 and multiplexer modules 30 to provide power to a cylindrical transducer array 32 surrounding a treatment cavity 34. The system 14 also includes a thermoelectric cooler 35 thermally coupled to the cylindrical transducer array 32 to control operating temperature of the cylindrical transducer array 32. Temperature control within the breast being treated is achieved by thermistor/thermometry subsystem 36 sensing breast temperatures through thermometry needles 38 inserted into the breast undergoing treatment. A receiver subsystem 40 receives temperature data from the thermistor thermometry subsystem 36 and power output data from the multiplexer modules 30, thereby enabling closed loop control of the temperature distribution in the breast being treated. These types of conventional closed loop control systems are illustrated, for example, in U.S. Pat. Nos. 4,311,154; 4,378,806; 4,638,436; 5,220,927 and 5,224,492. All of the figures and sections of these patents describing computer control system provide examples of the conventional state of the art, and these particular sections are incorporated by reference herein. Therefore, any one of these example computer control systems and associated ultrasound power sources and temperature monitoring systems can be used to effectuate the thermotherapy treatment provided herein, when used with the inventive combination in the apparatus 10.

Figure 3:
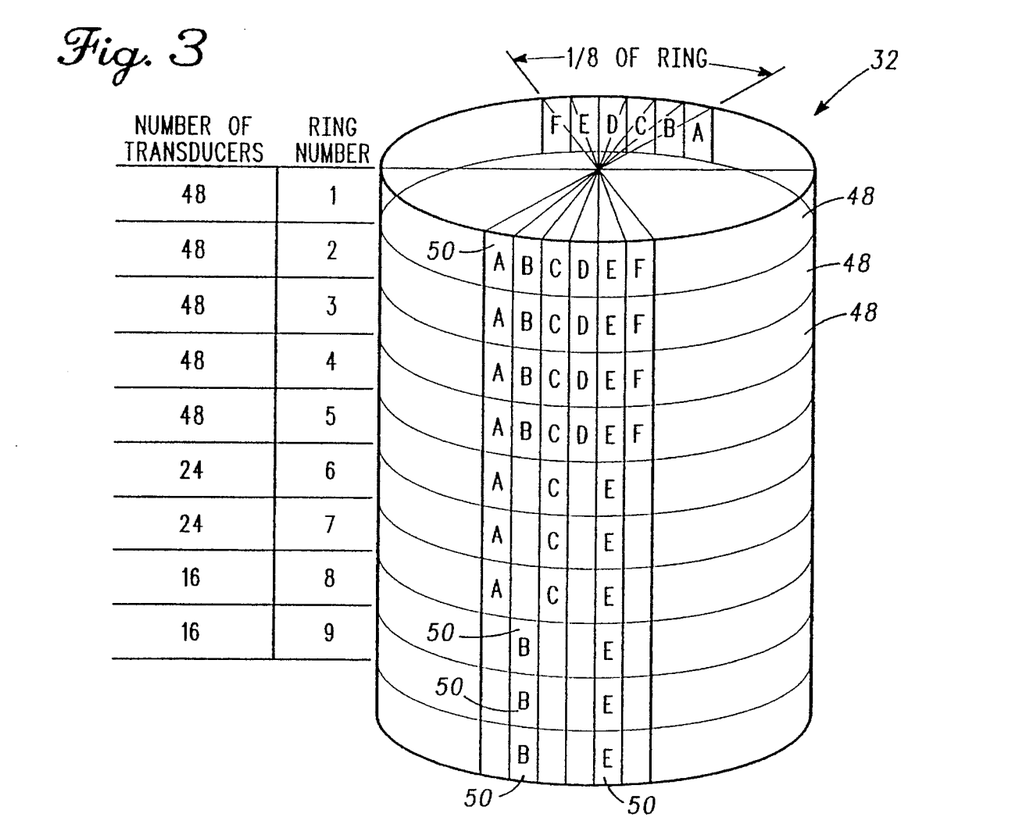
FIG. 3 illustrates a thermotherapy treatment device including a cylindrically shaped array of transducer rings.

The patient undergoing treatment reclines prone on treatment table 42 shown in FIG. 2. The patient is positioned such that the breast to be treated extends downward through a tapered opening 44 (to ensure presentation of the entire breast for treatment) and into cylindrical housing 46 embodying the cylindrical transducer array 32 (see FIG. 3). Preferably the cylindrical housing 46 contains water or other such appropriate coupling medium for the ultrasound being generated. This cylindrical transducer array 32 is disposed on the inner wall of the cylindrical housing 46 and is most preferably constructed of a plurality of cylindrical rings 48. In a preferred embodiment, each of these rings 48 are stacked on one another with watertight seals therebetween. Each of the rings 48 also includes a selectable number of active transducer elements 50 with the number of the active transducer elements 50 varying from a maximum in the treatment segment associated with the base of a breast adjacent the chest wall to a minimum at the top of the breast. In the illustrated cylindrical transducer array 32 of FIG. 3, the minimum number of active transducer elements 50 is sixteen, while the maximum is forty-eight. For purposes of clarity, only two of eight angular segments are shown for the individual elements 50. The illustrated arrangement is of course repeated along 360°. In the preferred embodiment of FIG. 3, the first five of these cylindrical rings 48 have forty-eight active ones of the transducer elements 50, the next two have twenty-four of the active transducer elements 50 and the last three have sixteen of the elements 50 along a full 360° of the cylindrical ring 48. Based on the analyses performed (see Examples), it is unnecessary to fill all the available ring locations with one of the active transducer elements 50. Table I below illustrates one preferred arrangement for the plurality of the cylindrical rings 48. Each of the transducer elements 50 is substantially square having dimensions of 1.5 cm×1.5 cm on a side. Spacing between the active transducer elements 50 along vertical dimensions is 2.4 mm. Consequently, the stacked cylindrical rings 48 accommodate breast lengths of 17 cm or less.

TABLE I

| | Arrangement of Active Transducers | | |
|---|---|---|---|
| Ring No. | FQ 1 (MHz)/ No. XDCRS | FQ 2 (MHz)/ No. XDCRS | Total XDCRS |
| 1 | 4.5/24 | 2.0/24 | 48 |
| 2 | 4.5/24 | 2.0/24 | 48 |
| 3 | 4.5/24 | 2.0/24 | 48 |
| 4 | 4.5/24 | 2.0/24 | 48 |
| 5 | 4.5/24 | 2.0/24 | 48 |

TABLE I-continued

| | Arrangement of Active Transducers | | |
|---|---|---|---|
| Ring No. | FQ 1 (MHz)/ No. XDCRS | FQ 2 (MHz)/ No. XDCRS | Total XDCRS |
| 6 | 4.5/12 | 2.0/12 | 24 |
| 7 | 4.5/12 | 2.0/12 | 24 |
| 8 | 4.5/12 | 2.0/4 | 16 |
| 9 | 4.5/16 | | 16 |
| 10 | 4.5/16 | | 16 |

In addition, the stacked cylindrical rings 48 can be rearranged to accommodate different breast sizes as detailed in Table II below:

TABLE II

Cylindrical Array Applicator Design
Total Cylinder I.D. = 25 cm
Transducers: 15 mm × 15 mm
Rings of Transducers: 10 (numbered from top down)
Each ⅛ ring vertical section driven by RF
Amplifiers whose outputs are multiplexed to "step around" ring

| Ring No. | No. Transducers | Breast Size (cm) Large | Breast Size (cm) Small | No. Transducers in ⅛ of ring |
|---|---|---|---|---|
| 1 | 48 | 16 | 8 | 6 |
| 2 | 48 | 14 | 7 | 6 |
| 3 | 48 | 12 | 6 | 6 |
| 4 | 48 | 10 | 5 | 6 |
| 5 | 48 | 8 | 4 | 6 |
| 6 | 24 | 7 | 3 | 3 |
| 7 | 24 | 6 | 2 | 3 |
| 8 | 16 | 4 | 0 | 2 |
| 9 | 16 | 3 | 0 | 2 |
| 10 | 16 | 0 | 0 | 2 |

Not only does the cylindrical transducer array 32 act to apply ultrasound power to the breast being treated, but also provides several monitoring functions as well. One such function concerns determination of breast contour and location of the breast within the treatment cavity 34. This function is accomplished by operating the active transducer element 50 in a diagnostic pulse-echo mode, which will be discussed later in more detail (see FIG. 8).

Figure 6:
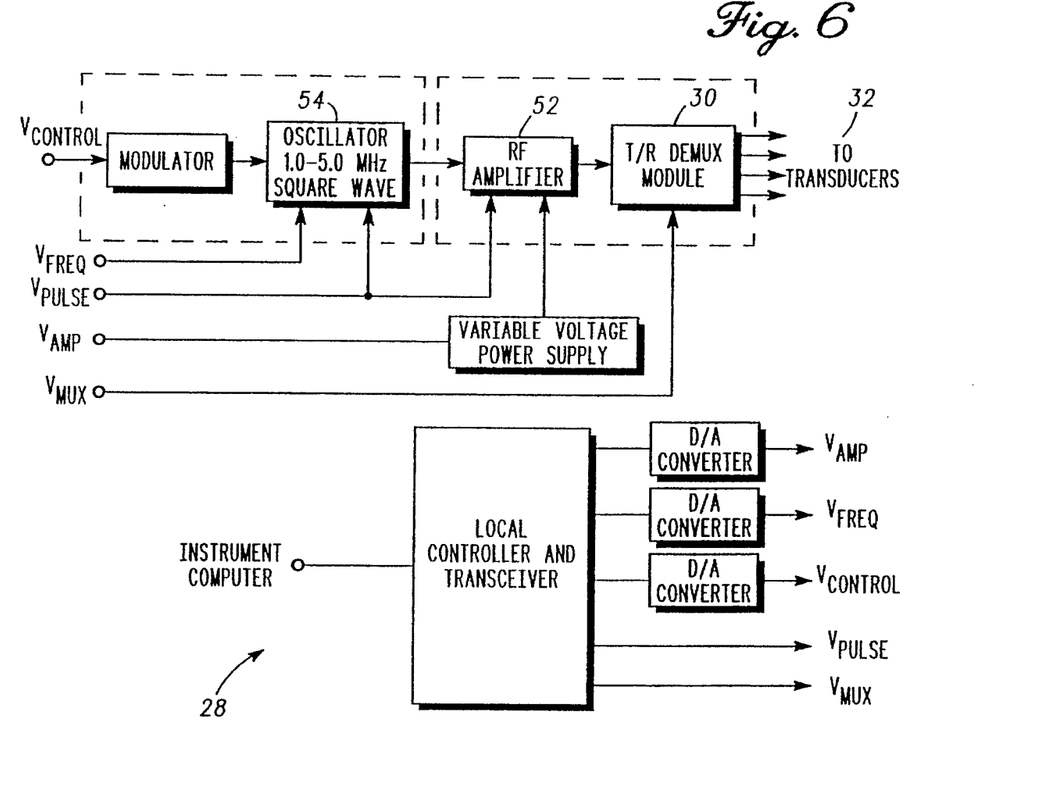
FIG. 6 illustrates an RF amplifier block diagram of a system for outputting power to the ultrasound transducers.

In a preferred embodiment, the RF power subsystem 28 mentioned hereinbefore and shown in FIGS. 1 and 6 includes eight independent RF amplifiers 52 driven by twenty separate oscillator sources 54. Each of the oscillator sources 54 includes a computer controlled voltage controlled oscillator ("VCO") operating over the 1–5 MHz frequency range and is used to drive four of the RF amplifiers 52. The individual VCOs can be frequency swept by as much as 250 kHz, plus or minus the VCO center frequency. The frequency sweep bandwidth is initially designed to be set manually (between 0 kHz and 250 kHz) on the mounting circuit board. Additional D/A channels can be added for computer control of the sweep bandwidth if needed. Each of the RF amplifiers 52 incorporates its own voltage control/regulator circuit which can provide independent computer control of output power level for each amplifier channel. Each output from the RF amplifiers 52 is coupled to the multiplexer modules 30 for output to the cylindrical transducer array 32.

Figure 7:
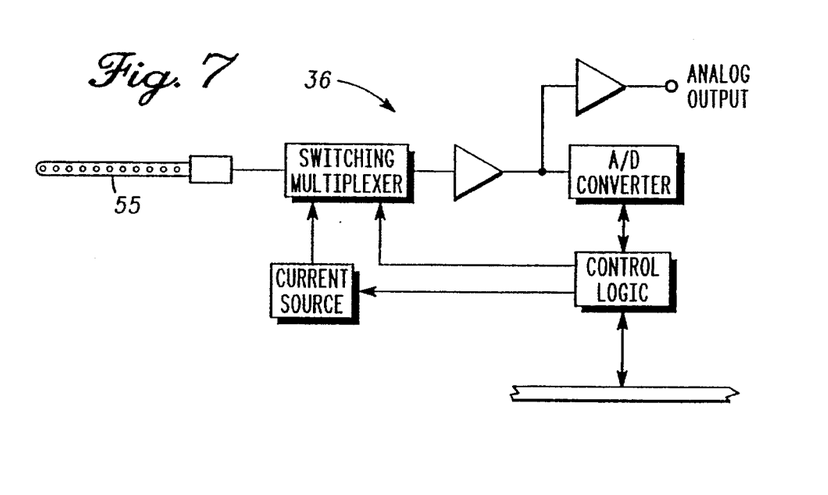
FIG. 7 illustrates a thermometry system block diagram.

The thermistor thermometry subsystem 36 (see FIGS. 1 and 7) is a conventional invasive temperature measurement device and is a conventional multi-channel thermistor based profilometer which provides a large number of sensor points within a single probe 55. The probes 55 used to measure interstitial temperatures are thermistors 56 mounted on needles 58 or can be molded into catheters or the like. In the most preferred embodiment, the subsystem 36 can drive up to eight of the multi-channel temperature probes 55. The subsystem 36 shown in FIG. 7 includes a medically isolated driver card 60, a control logic card 62 and an interface multiplexer 64.

Figure 8:
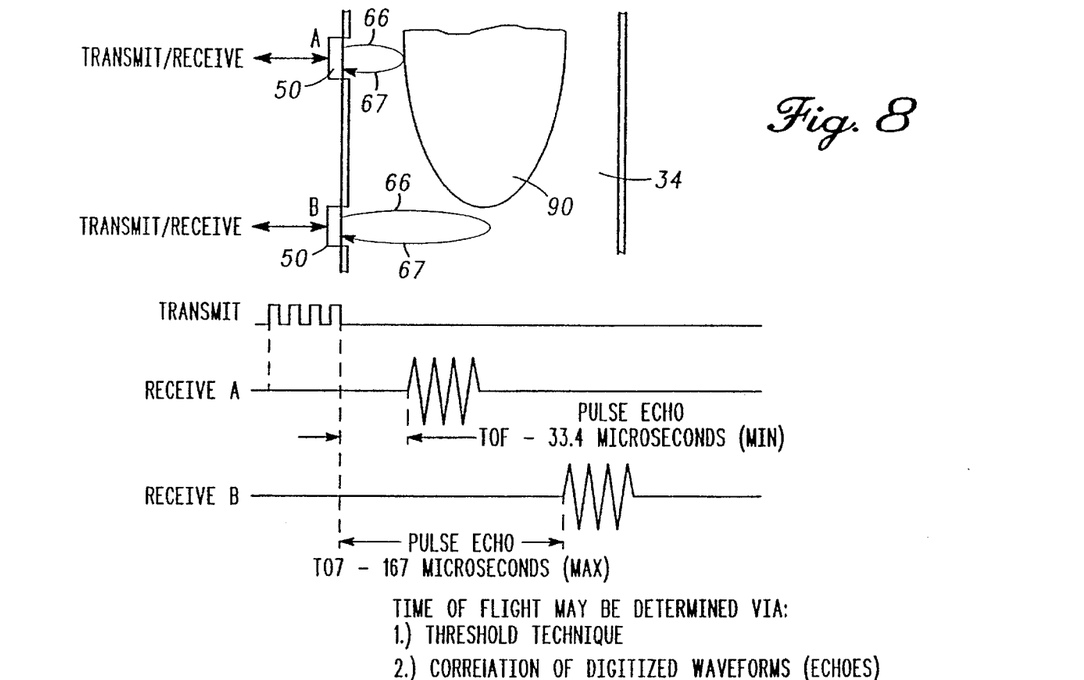
FIG. 8 schematically illustrates monitoring the contour of the patient's breast undergoing thermotherapy treatment in a treatment cavity.

Noninvasive monitoring can be carded out by means of the cylindrical transducer array 32. As shown in FIG. 8, pulse echo ultrasound data is collected by the instrument computer 26 and sent to a contour monitoring subsystem 33, which performs conventional time delay calculations to determine the distance to the exterior tissue surface which reflected the ultrasound. This subsystem 33 can convert the pulse echo data into three-dimensional image data which provides the operator with an outline of the contour of the breast being treated within the treatment cavity 34. Further, the subsystem 33 can map three-dimensional data into a two-dimensional or three-dimensional data projection suitable for display. This subsystem 33 also can provide information to a dynamic treatment calibration subsystem 37 to locate the patient's breast being treated within the treatment cavity 34 relative to the cylindrical transducer array 32. Therefore, as shown in FIG. 8, noninvasive contour monitoring can be performed by selecting a single one of the active transducer elements 50 to transmit an ultrasound pulse 66 into the treatment cavity 34 and then receiving a reflected form 67 of the ultrasound pulse 66 while measuring the time required for return of the ultrasound pulse 66. The spatial resolution of such a pulse echo technique is about 2 mm. By pulsing a representative, large number of the active transducer elements 50 (and sending the return echo), a three-dimensional contour map of the target breast tissue can be located in the treatment cavity 34 relative to the cylindrical transducer array 32.

Figure 5:
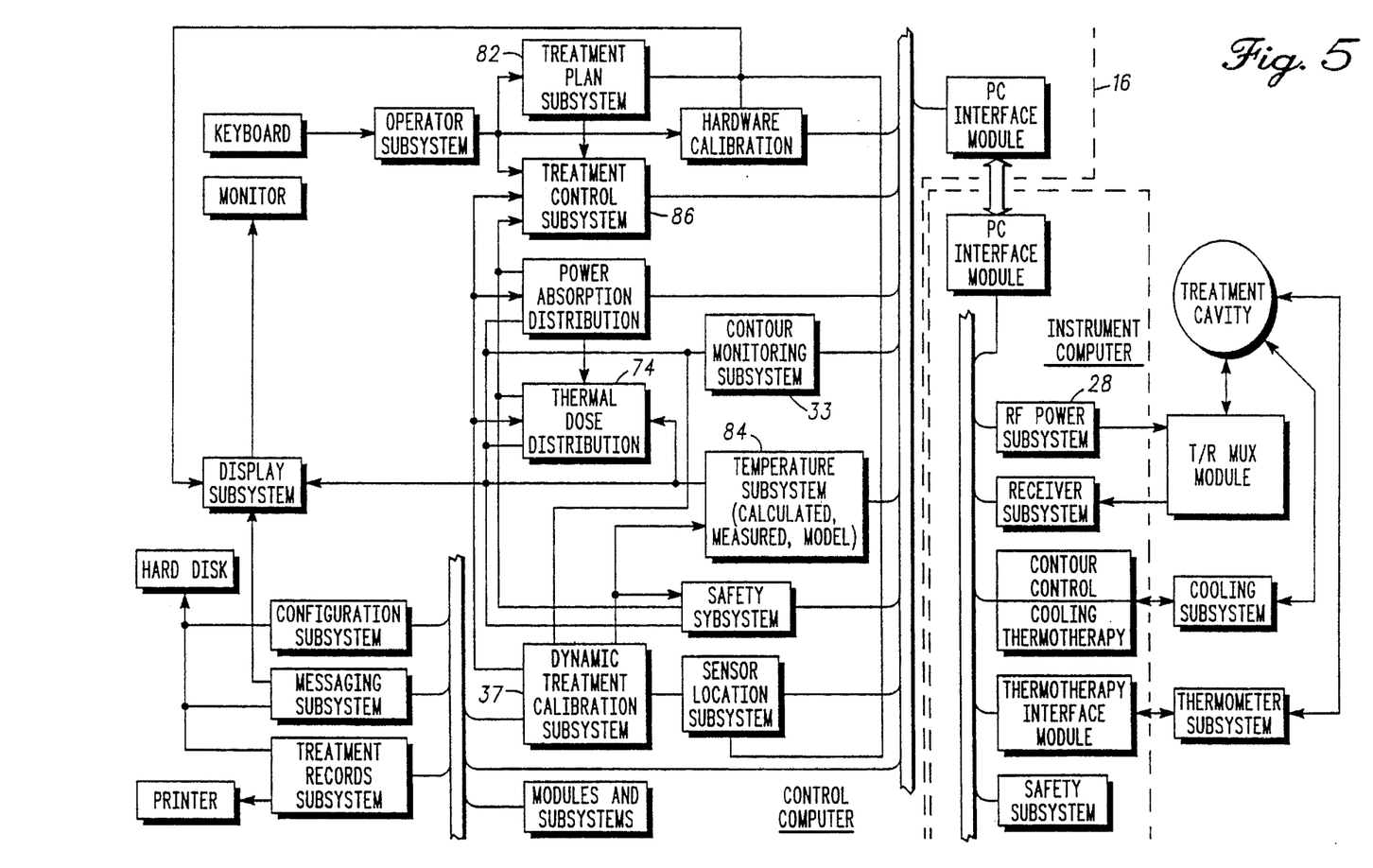
FIG. 5 illustrates a block diagram of the computer control system for thermotherapy treatment.
Figure 9:
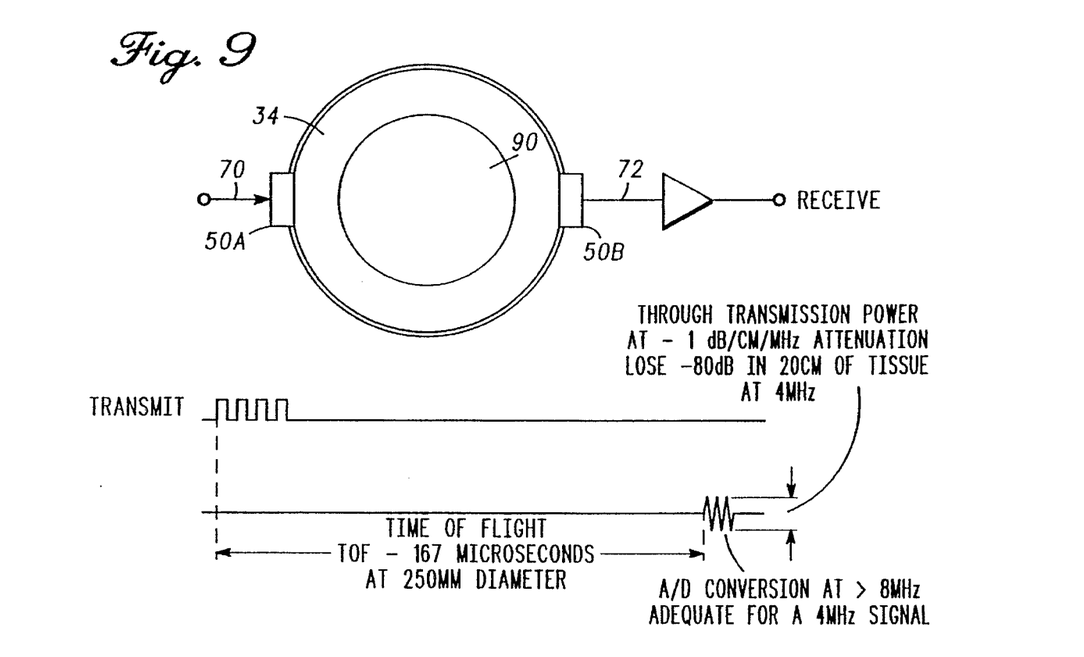
FIG. 9 schematically illustrates the determination of power transmitted through a breast undergoing thermotherapy treatment.

Monitoring of power absorption and attenuation of the ultrasound power in the patient's breast being treated can be accomplished by a variety of conventional methodologies. In FIG. 5 is schematically illustrated a closed loop control system using computer software embodied in power absorption distribution subsystem 68. This computer control system uses the known power output, the detected power and absorption to carry out all the necessary calculations. For example, as shown in FIG. 9, an ultrasound wave 70 is emitted by one of the transducer elements 50A, ultrasound enters the intervening breast tissue and any nonabsorbed ultrasound wave 72 is detected by another of the transducer elements 50B disposed opposite the element 50A. The resulting detected (transmitted through the tissue) signal is output to the control computer 16 which calculates power absorption in a conventional manner using the software of the power absorption distribution subsystem 68. This exercise can be repeated for a plurality of such pairs of the transducer elements 50A/50B to determine the power absorption throughout the treatment cavity 34. This information is then output to thermal dose distribution subsystem 74 which carries out the calculations to assure the level of power absorbed is in compliance with the treatment protocol selected.

Computer Control System

Closed loop computer control of the apparatus 10 mentioned hereinbefore is accomplished using the control computer 16 and the instrument computer 26. Such control systems can be effectuated using well-known, conventional computer software. As shown in FIG. 5, the control computer 16 generally provides an operator control interface, data measurement interpretation, feedback control and data recording by executing the computer software associated with a variety of subsystems shown in block diagram form. The instrument computer 26 shown in FIG. 5 generally provides direct hardware interfacing for collecting temperature measurements and data from transducer receivers, setting control output levels and controlling the timing for multiplexing of the cylindrical transducer array 32.

More particularly, the control computer 16 enables implementation of operator inputs entered by the keyboard 18 or use of the mouse 20 in conjunction with information displayed on the monitor 22. Operator control of the basic treatment protocol is maintained with feedback data provided to the operator as the protocol progresses. Actual control over the timing, power levels and RF frequencies applied to the plurality of the transducer elements 50 must be controlled very rapidly. Therefore, in order to accomplish these functionalities, rather than relying on manual control, the control Computer 16 controls the apparatus 10 as shown in the block diagram in FIG. 5. In the most preferred embodiment, the monitor 22 will provide displays to the operator of (1) a patient's breast contour every 1–5 seconds, (2) images of the temperature probes 55, (3) two-dimensional cross sections and three dimensional images of the patient's breast being treated, each with overlays of calculated isotherms, (4) providing alerts of developing hot spots, (5) a display of two-dimensional cross sections by selected location, and (6) continuous time and temperature monitoring displayed as a graph for each cross section as described in (5) above.

The control computer 16 also carries out the program in treatment plan subsystem 80. The subsystem 80 requests information from the operator for treatment operation. Such information includes the number of temperature probes 55, the number of sensors for the probe 55, spacing of the sensors on the probe 55, target temperature, temperature limits for each of the individual sensors and/or subregions undergoing treatment, patient name and/or number identifier. The treatment plan information is available as data via the control computer 16 to the other subsystems.

The control computer 16 further executes the programs of the treatment control subsystem 86 to modify transducer output power and RF frequency output based on information received from the power absorption distribution subsystem 68, the thermal dose distribution subsystem 74, a treatment plan subsystem 82, the dynamic treatment calibration subsystem 37 and a temperature subsystem 84. Once the output power and RF frequency settings have been determined, the treatment control subsystem 86 sends these data to the RF power subsystem 28 via the pc interface module 86 to enable actual power changes to be made for the transducer elements 50. Again, this manner of closed loop control can be carried out by any conventional computer control system, such as by the system described in incorporated U.S. Pat. No. 4,638, 436 or the other cited U.S. patents.

The treatment control subsystem 86 operates on a predefined treatment cell volume 94 (see FIG. 10) of the patient's breast. The actual volume of each of the treatment cell volumes 94 can be determined by a configuration subsystem data file stored in conjunction with the control computer 16. Most preferably the treatment cell volumes 94 are substantially of the same absolute volume, while still cumulatively encompassing the entire volume of the cylindrical housing 46. The temperature subsystem 84 collects temperature values for all the temperature sensors (such as the probes 55) and also performs temperature assessments from variation of time of flight (and thus velocity change by also knowing the distance between transducer output element 50A and transducer element sensor 50B—see FIG. 9) and amplitude degradation (note attenuation of the through-transmission power at right bottom part of FIG. 9) for ultrasound passed through the patient's breast 90 [(see FIG. 9 at bottom)]. These measurements can be performed for each of the treatment cell volumes 100. Invasive temperature measurements using the probes 55 and time of flight/ amplitude degradation measurements occupying the same volume 100 can be set equal and all derived temperatures in the neighboring volumes 100 can be calibrated according to the nearest invasive probe 55.

Figure 10A:
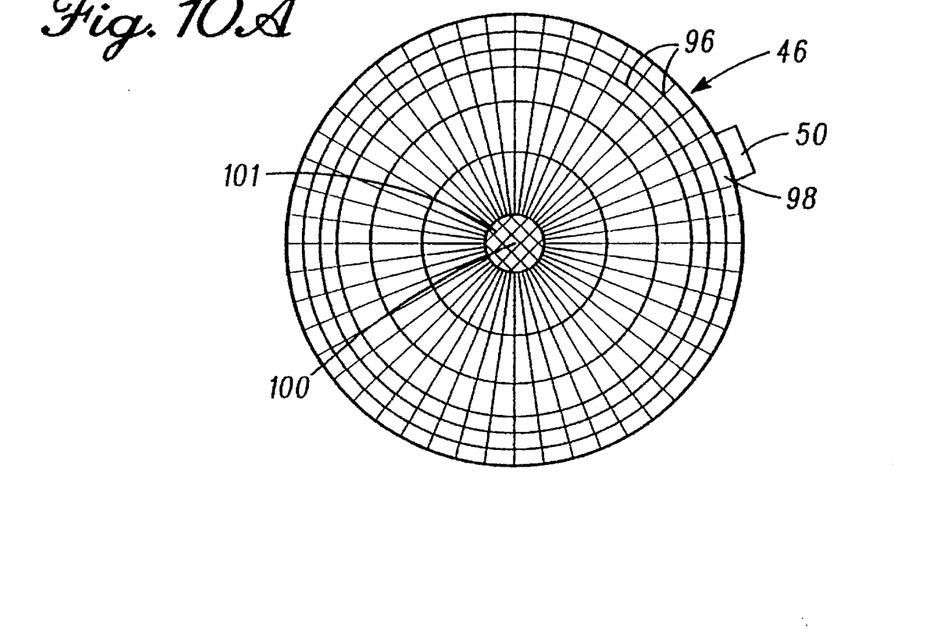
FIG. 10A is a top view of a cylindrical volume of treatment cells.
Figure 10B:
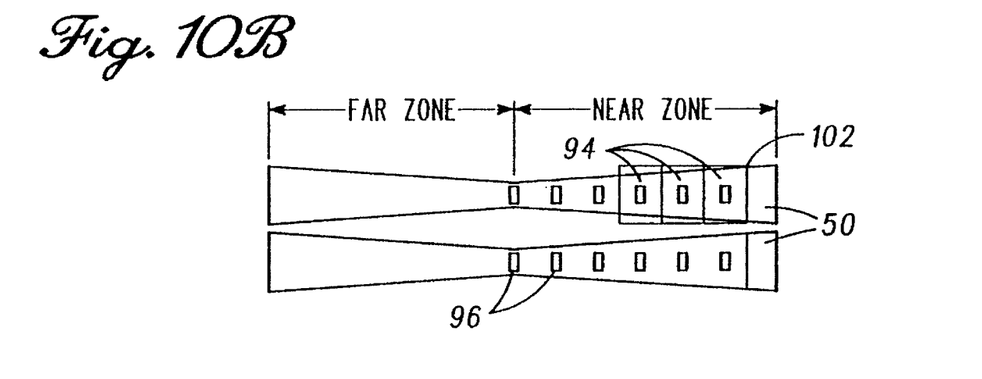
FIG. 10B is a side view of several rings of the cylindrical volume of FIG. 10A
Figure 10C:
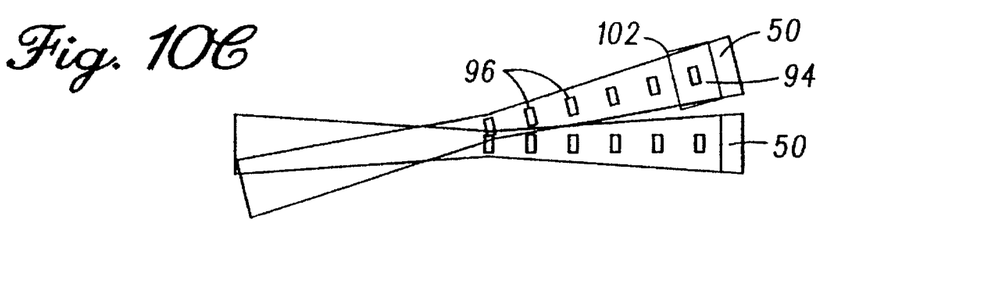
FIG. 10C is a top view of several angular segments of treatment cell volumes.

The center points 96, volume corner locations, and the transducer elements 50 affecting the treatment cell volume 94 are stored in a treatment cell information data file. FIG. 10 shows several views of the treatment cell volumes 94 in the cylindrical housing 46 and illustrates how the center points 96 are determined for a single one of the rings 48 of the transducers 50. Each of the treatment cell volumes 94 has its centerpoint 96 located on a line 98 from the center of the face of the transducer 50 to the centerpoint of the cylindrical housing 46. A center treatment cell volume 101 is actually a cylinder with a radius selected such that the volume 101 will match the volume value in the information data file. The remainder of the treatment cell volumes 94 for a given one of the transducer rings 48 are in the shape of a rhombus. Once the location of one of the center treatment cell volumes 100 has been determined, the radius value for the center points 96 of the rest of the volumes 100 are calculated and centers determined. Next, eight corner points 102 are calculated to identify unambiguously each of the treatment cell volumes 100. After all these volumes 100 have been characterized, each of the volumes 100 are checked to sort them into "near cell" or "far cell" zones of the field of view of the transducers 50. The control subsystem 86 therefore creates a list for each of the volumes 100 for all the transducers 50 which provide ultrasound to the volumes 100 and considering whether the ultrasound is in the "near zone" or "far zone."

If a volume defined in the configuration file for the treatment cell volume 94 does not match the volume 94 used to calculate the current treatment cell information file, the treatment control subsystem 86 will generate a new treatment cell information file. The treatment control subsystem 86 will operate in an automatic mode, but it will allow the controller to make manual adjustments of the temperature set points for each treatment cell volume during the treatment. The default mode will be to maintain tissue temperature at 43° C. in the treatment volume cells.

The following nonlimiting calculational example describes various aspects of the invention during use for thermotherapy therapy.

EXAMPLE

Figure 4A:
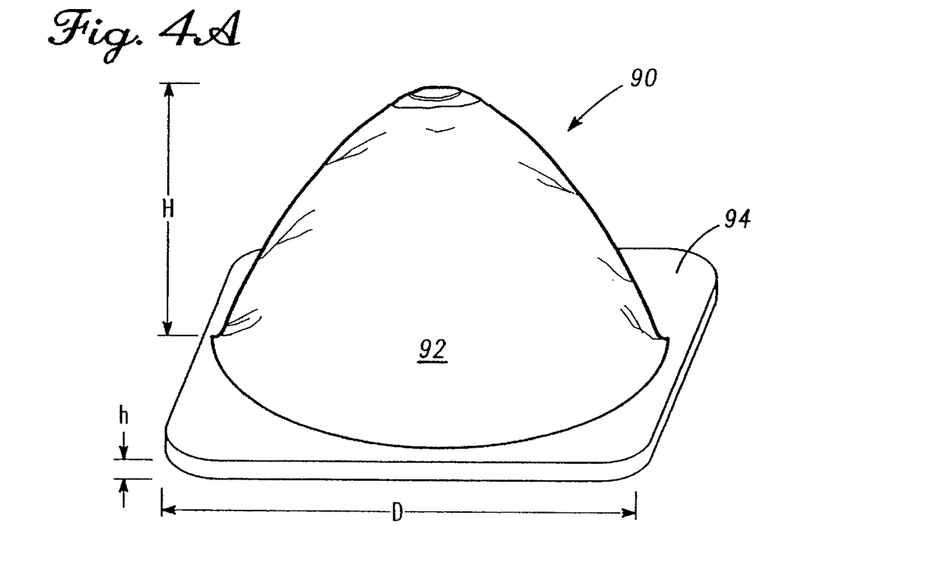
FIG. 4A illustrates a computerized theoretical breast model.

In performing calculations of the anticipated temperature profiles created by thermotherapy treatment, a geometric model of a patient's breast 90 was generated (seal FIG. 4A). The breast surface 92 was assumed to be a parabola with a height of H cm and a diameter of D cm at the base. The clinically relevant breast sizes, with the patient prone and the breast submerged into the water, filled a cylindrical housing 46 (see FIG. 2), were determined by measuring the sizes from volunteer patients in a clinic. The data showed that the average breast in a prone position was 11 cm long with a maximum diameter at chest wall 94 of 12 cm The maximum breast dimensions in the group of ten patients was 15 cm long and 15 cm in diameter. The temperature conditions at the external breast surface 92 can be controlled by adjusting the temperature of the water inside the cylindrical applicator. The temperature border condition at the chest wall is assumed to be 37° C. at a depth of hem below the chest wall 94. The parameters H, D and h are listed hereinafter in Table III together with several other important ultrasound interaction parameters, including attenuation, conductivity and perfusion.

There is a significant normal variation in the numerical values of ultrasound interaction parameters and heat transfer parameters in tissue. There is also a great deal of uncertainty in these values. We have determined a range of operating characteristics of the breast applicator accounting for these variations and uncertainties by using computer simulations. We have concluded that it is most preferable to use a dual frequency transducer array 32. A low ultrasound frequency, in the range of 1.5–2.5 MHz, is needed to compensate for the heat removed by the blood flow and permits an initial quick temperature elevation at depth in the breast tissue. Due to considerable uncertainty in the breast tissue attenuation, a broad frequency band for the low frequency transducers is desired. A high frequency form of the transducer elements 50, in the range of 4–4.5 MHz, is needed to maintain a steep temperature gradient near the surface of the target volume. In these models, the high and low frequency transducer elements 50 are mounted alternatively in each one of the cylindrical rings 48. Each one of the rings 48 offers power and frequency control sufficient to heat the whole breast or a quadrant of the breast to a minimum of 42° C., but not exceeding 44° C.

TABLE III

| Parameters used in the model. | | |
| --- | --- | --- |
| Parameter [Ref.] | Default value | Range studied |
| Attenuation breast | 0.086 ($f^{1.5}$ Np, cm$^{-1}$) | 0.052–0.12 |
| Attenuation water | 0.0002 ($f^2$ Np, cm$^{-1}$) | 0.0002 |
| Conductivity | 0.5 (W, m$^{-1}$, K$^{-1}$) | 0.4–0.8 |
| Perfusion, | 30 at 37° C. 100 at 44° C. (ml, Kg$^{-1}$, min$^{-1}$) | 30–100 30–20 |
| $T_{water}$, °C. | 37° C. | 30° C.–40° C. |
| D, cm | 15 | 10–15 |
| H, cm | 8 | 5–8 |
| h, cm | 0.9 | 0–1.2 |

The second part of the model calculates the energy deposition in the patient's breast tissue resulting from absorption of ultrasound energy. The ultrasound is assumed to originate from a continuous wave (CW) rectangular plane source. In this method, the plane source is divided into rectangular elements, surrounded by a rigid baffle. The elements are chosen to be small and the far field approximation is valid at all points of interest. The method sums contributions from these small elements to a given field point. The model is limited by only allowing one medium for the calculations. However, we have modified the conventional Ocheltree model to allow two media, namely the water in the cylindrical housing 46 and the breast tissue submerged into the water. This modification is possible under the assumption that the physical density and the speed of sound for water and breast tissue are very close so that their acoustic impedance is about the same. With about the same acoustic impedance between breast tissue and water, the energy loss due to ultrasound reflection from the breast surface 92 can be substantially ignored. Reflection from breast tissue has been measured to be about −40 dB, which suggest that our assumption is quite reasonable. It also means that the acoustic impedance match between water and breast tissue is excellent and that very little energy is reflected away from the breast surface.

Under the condition of good acoustic impedance match we can follow the same arguments as used in the deduction of the Ocheltree formula for one medium, except a change of the exponential decay factor from $e^{-ar-jkr}$ to $e^{-1_sr_w-a_br_b-jkr_w-jkr_b}$, where a is the attenuation coefficient and r is the distance between the field point to the elemental areas of the planar source and k is the wave number. The values $a_w$ and $a_b$ are the attenuation coefficients in water and the breast 90. The values of $r_w+r_b$ is the distance from the field point to the planar source; and the values of $r_w$ and $r_b$ are the distance in water and breast tissue respectively. For a uniformly excited rectangular planar source, the sound pressure amplitude $P_0$ at a point inside the breast 90 is given by a summation of complex terms, representing the pressure due to a rectangular elemental source.

$$P_0 = \frac{j\rho\Delta A}{\lambda} \cdot \sum_{n=1}^{N} \frac{u}{R} \cdot e^{-(\alpha_w r_w + \alpha_b r_b + jkr_w + jkr_b)}$$

$$\sin c\left(\frac{kx'_n\Delta w}{2(r_w+r_b)}\right) \cdot \sin c\left(\frac{ky'_n\Delta w}{2(r_w+r_b)}\right)$$

$\rho$ is the density, c is the phase velocity of the sound waves, u is the complex surface velocity for all the elements, $\lambda$ is the wavelength, $\Delta A - \Delta h x \Delta w$ is the elements size, $x_n^1$ and $y_n^1$ are the coordinates of the field point with respect to the center of the element n.

The SAR (specific absorption rate) deposited by the transducer array 32 inside the breast 90 can be calculated from the sound pressure amplitude $P_0$ at the point:

$$SAR = \frac{\alpha_b \cdot P_0^2}{\rho \cdot c}$$

The breast volume is divided into voxels and the SAR, is calculated to the center of each voxel. These voxels are also used in the thermal calculation, which will be discussed in the following paragraph. The SAR in each voxel is normalized to the total energy deposited inside the breast from all the transducers. The total SAR in the field point is the arithmetic sum of that contributed by each of the transducer elements 50.

The third part of the model provides a solution to the standard bio-heat transfer equation. Such solutions result in temperature distributions as a function of time in the breast tissue.

It is convenient to write the bio-heat transfer equation $$\frac{\partial T}{\partial t} = (K/c_v)\nabla^2 T - (T-T_0)/\tau + q_v/c_v$$

T is the temperature and $T_O$ is the body temperature, i.e. 37° C. K is the thermal conductivity coefficient (w, $m^{-1}$, $K^{-1}$), $C_v$ is the heat capacity per unit volume (J, $g^{-1}$, $K^{-1}$), $q_v$ is the heat production rate per unit volume (W, $kg^{-1}$), i.e., SAIL $\tau$ is the perfusion constant (s), which most commonly is expressed as perfusion rate (ml, $Kg^{-1}$, $min^{-1}$), where $\tau=p\times c_v\times(w\times c_{vb})^{-1}$.

The usefulness and limitations of this model has been discussed by a number of persons skilled in the art. A major limitation of this model is the incorporation of perfusion resulting from the blood flow. However, for breast tissue, we assume that perfusion is not the dominating factor, due to absence of large blood vessels. Therefore, we believe that the bio-heat transfer model shown above is reasonable.

The finite difference method is used in the three-dimensional numerical calculation. This method gives a great deal of flexibility to deal with different geometries and boundary conditions. Starting from a given initial condition the temperature evolution for a whole treatment session can be simulated. A voxel size of 2×2×2 mm³ or 3×3×3 mm³ is used for the two breast sizes listed in Table II. This matrix size is a compromise between an acceptable accuracy and reasonable CPU time required. The calculation of T is performed at every three second interval. This time step is sufficiently small to satisfy the temperature stability criteria.

The tissue parameters listed in Table III are based on the published data. To perform the calculations, we used perfusion data for resting muscle tissue. In this model, the perfusion rate is increasing linearly by a factor of three when the temperature is elevated from 37° C. to 44° C.

The initial temperature inside the breast 90 is assumed to be 37° C. uniformly. Near the surface 92 the temperature in the water can be adjusted and maintained at any value between 30° C. and 40° C. Again, at depth h cm below the chest wall 94, the temperature is assumed being always maintained at 37° C.

The computer model calculates the SAP, and temperature distribution at three minutes interval during the complete treatment simulation. Initially the default values in Table III are used for the treatment simulation.

The range of values shown in the third column of Table III is then used to determine the optimal operating characteristics and design specifications of the breast applicator. The range of values account for uncertainties and normal variations in these parameters.

Figure 4B:
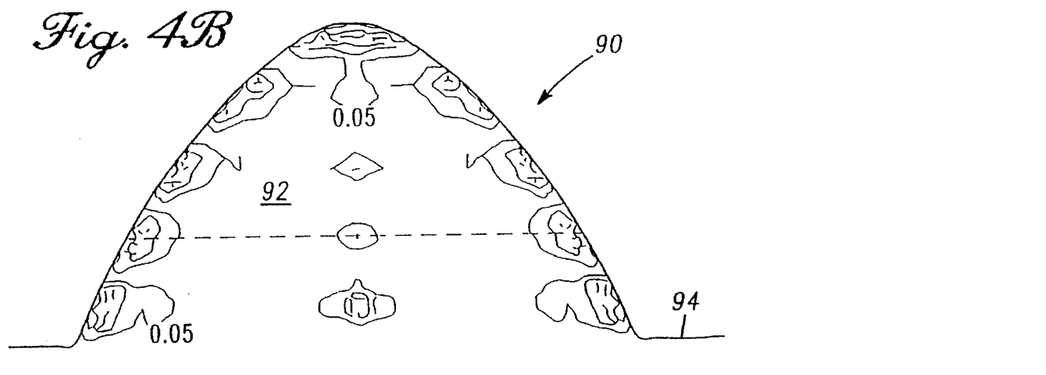
FIG. 4B illustrates a side view of absorbed power distribution for the breast for maintaining steady state temperatures of 42°–44° C.
Figure 4C:
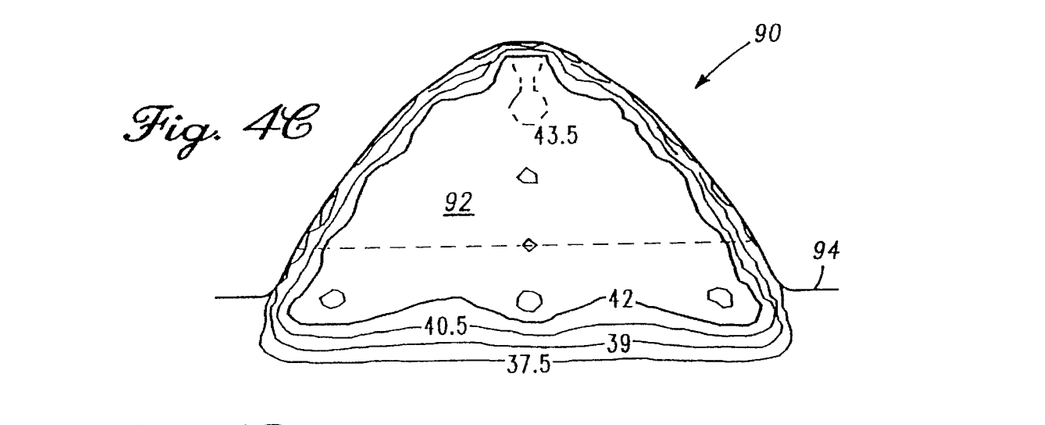
FIG. 4C shows the steady state temperatures corresponding to the power distribution of FIG. 4B.

As seen in FIG. 2A, the cylindrical transducer rings 48 are stacked to form the cylindrical housing 46 into which the breast 90 is submerged. The power deposition m a certain point in the breast 90 is delivered primarily from the ring 48 that defines the plane in which the point is located. The control of the temperature at that point is thus, to a first approximation, reduced to control of the power deposition within each of the rings 48. This is seen in FIG. 4B, where the SAR distribution show five distinct cross-sectional planes, each plane defined by the individual ones of the cylindrical rings 48. As shown in the lower panel of FIG. 4C, at steady state temperature, most of the breast tissue is surrounded by the 42° C. iso-temperature line and the maximum temperature is 43.7° C.

Figure 4D:
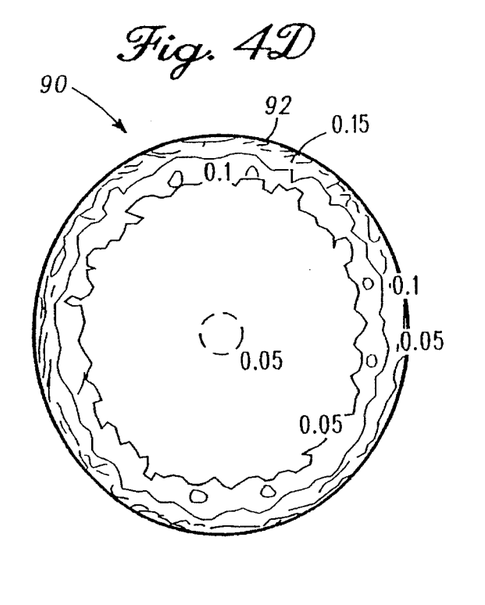
FIG. 4D illustrates a top view of the power distribution of FIG. 4B.
Figure 4E:
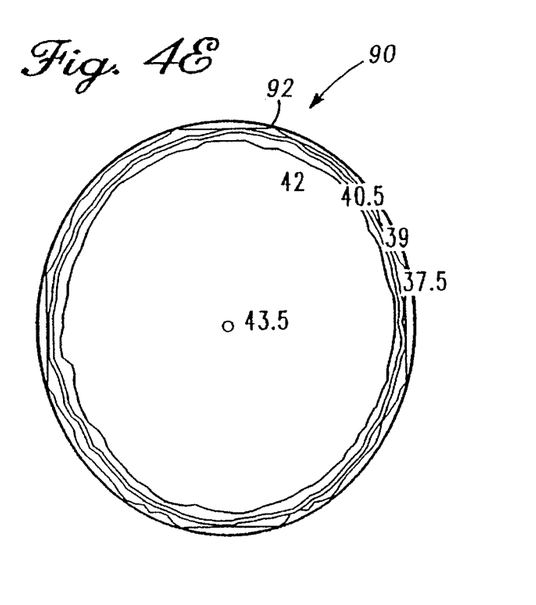
FIG. 4E shows a top view of the temperature distribution of FIG. 4C.
Figures 4F, 4G, 4H, 4I, 4J:
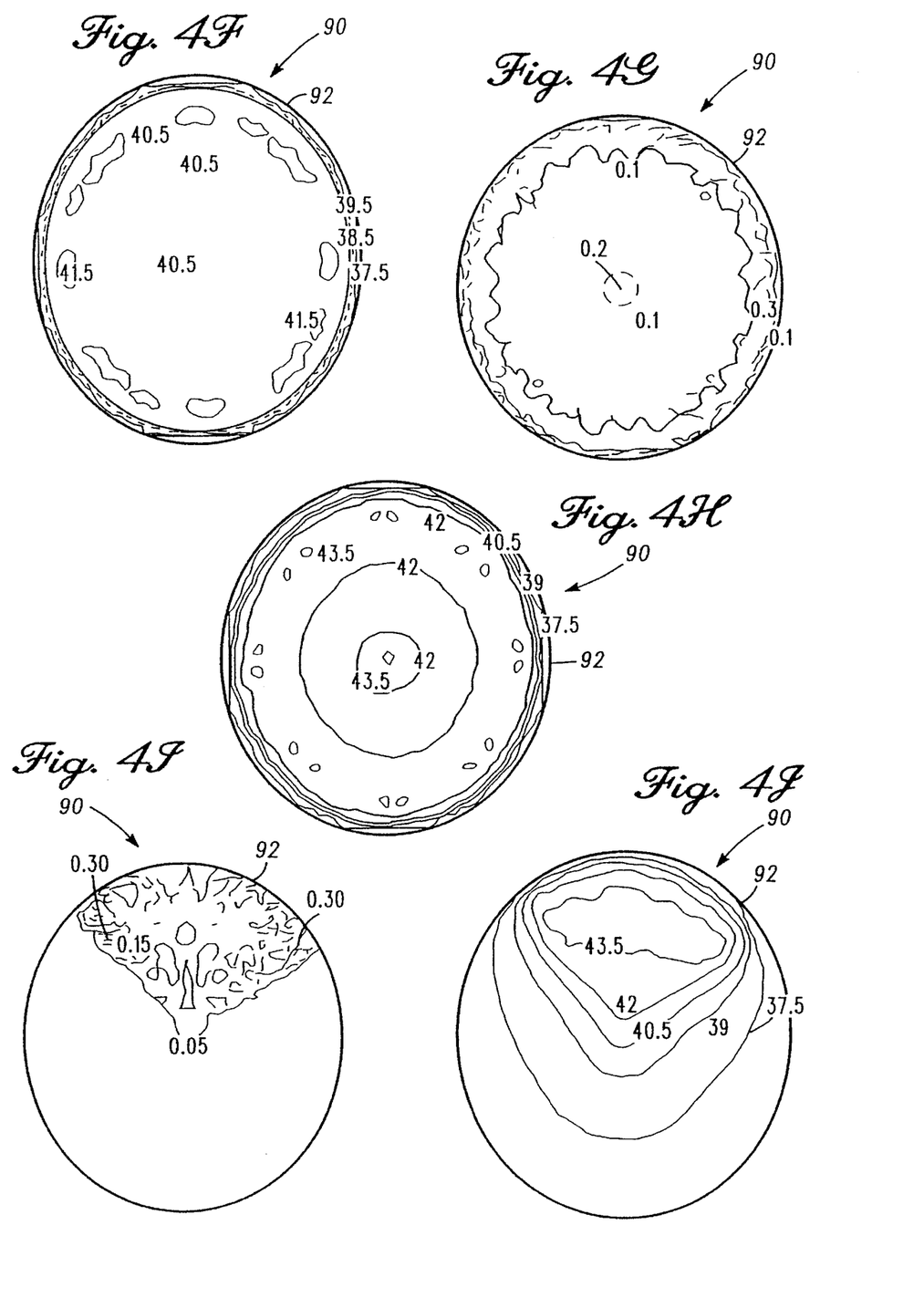
FIG. 4F shows a top view of temperature distribution for the power distribution of FIG. 4B, but with different perfusion values than FIG. 4E.
FIG. 4G shows a top view of applied power distribution for the breast with increased perfusion rates compared to FIG. 4B.
FIG. 4H shows the resulting steady state temperature distribution for the applied power in FIG. 4G.
FIG. 4I shows a top view of applied power distribution for maintaining temperature between 42°–44° C. for treatment of one breast quadrant.
FIG. 4J shows the resulting steady state temperature distribution for the applied power of FIG. 4I.

Breast tissue perfusion rate and its dependence on the temperature and other physiological factors determine the choice of ultrasound frequency and power. However, it is desirable to test the effect of increased perfusion rate on the ability to control the equilibrium temperature distribution. If we increase the perfusion rate to 100 ml, $kg^{-1}$, $min^{-1}$ at 37° C. and 200 ml, $kg^{-1}$, $min^{-1}$ at 44° C., and if we maintain the same SAR distribution as shown in FIG. 4D, than the corresponding equilibrium temperature distribution is shown in FIG. 4F. The temperature distribution show heterogeneity and does not reach the required 42° C.$\leq$T$\leq$44° C.

To achieve an acceptable equilibrium temperature distribution, under this high perfusion rate, we need to increase the SAP, distribution. In FIG. 4G is shown the SAR distribution, which results in an acceptable equilibrium temperature distribution, 42° C.$\leq$T$\leq$44° C. (see FIG. 4H).

In FIG. 4I is illustrated the ability to heat a quadrant of the breast. It is achieved by depositing energy in the periphery of the target volume using a proper mix of high and low frequency ultrasound. FIG. 4J is a resulting temperature distribution for treatment of a quadrant of a breast.

While preferred embodiments of the invention have been shown and described, it will be clear to those skilled in the art that various changes and modifications can be made without departing from the invention in its broader aspects as set forth in the claims provided hereinafter.

What is claimed is:

1. A thermotherapy treatment apparatus having ultrasound transducers for applying ultrasound energy to a patient treatment site, comprising:

means for providing radio frequency power to said ultrasound transducers;

means for measuring temperature of the patient treatment site; and means for controlling radio frequency power being provided to said ultrasound transducers responsive to temperatures being measured by said means for measuring temperature, said ultrasound transducers forming a plurality of cylindrical transducer element rings stacked to form a treatment cavity for encompassing the patient treatment site.

2. The thermotherapy treatment apparatus as defined in claim 1 wherein said plurality of said cylindrical transducer element rings comprises individual rings having a different number of individual ultrasound transducers making up each of said rings than other ones of said rings.

3. The thermotherapy treatment apparatus as defined in claim 1 wherein said transducers can be powered at different radio frequencies.

4. The thermotherapy treatment apparatus as defined in claim 3 wherein each of said transducer elements rings consists of an even number of said ultrasound transducers.

5. The thermotherapy treatment apparatus as defined in claim 4 wherein said ultrasound transducers are operated at two different radio frequency bands and within each of said transducer element rings every other one of said ultrasound transducers are driven by the same radio frequency band.

6. The thermotherapy treatment apparatus as defined in claim 5 wherein said ultrasound transducers are operated at two different radio frequency bands consisting of 1.5–2.5 MHz and 4.0–4.5 MHz.

7. The thermotherapy treatment apparatus as defined in claim 6 wherein selected ones of said transducer rings comprise 48 different ones of said ultrasound transducers with 24 thereof operated at one radio frequency band and the remaining 24 of said ultrasound transducers operated at another radio frequency band.

8. The Thermotherapy treatment apparatus as defined in claim 1 further including means for activating selected transducers in each of said transducer element rings.

9. The thermotherapy treatment apparatus as defined in claim 1 further including means for delivering the ultrasound energy from said transducer element rings defining a plane in which a certain point of the patient treatment site is located.

10. The thermotherapy treatment apparatus as defined in claim 9, further comprising a computer for controlling said means for delivering the ultrasound energy.

11. The thermotherapy apparatus as defined in claim 9 wherein said means for delivering the ultrasound energy to selected rings further operates to choose selected ones of said ultrasound transducers in each of said transducer element rings to output the ultrasound energy.

12. A method of performing thermotherapy treatment on a patient treatment site, comprising:

providing cylindrically stacked transducer element rings having a plurality of transducers for generating ultrasound waves as an output;

providing radio frequency power to said ultrasound transducer element rings to generate the ultrasound waves for heating the patient treatment site and also for intermittently generating the ultrasound waves for reflecting the ultrasound waves from the exterior of the patient treatment site, thereby enabling measurement of the location of the patient treatment site being treated;

measuring temperature of the patient treatment site increased responsive to irradiation by the ultrasound waves;

controlling radio frequency power provided to said ultrasound transducers, said transducers being arranged as a plurality of individual elements forming a treatment cylinder for the patient treatment site.

13. The method as defined in claim 12 further including the step of determining therapy temperature of the patient treatment site by performing selectively time of flight and pulse amplitude measurements on the ultrasound waves passed through the patient treatment site.

14. The method as defined in claim 12 further including varying the number of activated ones of said ultrasound transducers, thereby varying the temperature contour applied to the patient treatment site.

15. The method as defined in claim 12 wherein the step of measuring temperature of the patient treatment site comprises intermittently measuring change of velocity of the ultrasound waves passed through the patient treatment site.

16. The method as defined in claim 15 wherein measuring the change of amplitude of the ultrasound waves comprises using oppositely disposed transducers in at least one of said transducer element rings.

17. The method as defined in claim 12 further including the step of measuring ultrasound wave absorption by the patient's tissue by measuring attenuation of power output from selected ones of ultrasound transducers in said transducer element rings.

18. The method as defined in claim 12 further including the step of obtaining a three-dimensional spatial map for the patient treatment site from the ultrasound waves by accumulating information from said ultrasound waves reflected from the patient treatment site.

19. The method as defined in claim 18 wherein determining the three-dimensional data map comprises individually pulsing selected ones of said ultrasound transducers and detecting at least one of a reflected and transmitted ultrasound wave by said selected ones of said ultrasound transducers.

20. A thermotherapy treatment apparatus having ultrasound transducers for applying ultrasound energy to a patient treatment site, comprising;

means for providing radio frequency power to said ultrasound transducers;

means for measuring temperature of the patient treatment site;

means for controlling radio frequency power being provided to said ultrasound transducers responsive to temperature being measured by said means for measuring temperature, said ultrasound transducers forming a plurality of cylindrical transducer element rings stacked to form a treatment cavity for encompassing the patient treatment site; and means for intermittently activating a selected ultrasound transducer for obtaining a three-dimensional map of the patient treatment site, said selected ultrasound transducer upon activation generating an ultrasound wave pulse and at least one of said ultrasound transducers sensing at least one of a transmitted and a reflected ultrasound wave pulse.

* * * * *